United States Patent [19]

Rebold

[11] 3,977,079

[45] Aug. 31, 1976

[54] KNIFE HAVING EASILY REMOVABLE BLADE

[75] Inventor: Jerome I. Rebold, Timonium, Md.

[73] Assignee: CBS Inc., New York, N.Y.

[22] Filed: Nov. 12, 1975

[21] Appl. No.: 631,209

[52] U.S. Cl. .................................. 30/336; 279/51; 294/100
[51] Int. Cl.² ........................................ B26B 1/00
[58] Field of Search ............ 30/329, 334, 336, 337, 30/338; 279/41, 51, 43, 53; 81/116, 128; 294/100; 128/305

[56] References Cited
UNITED STATES PATENTS

| | | | |
|---|---|---|---|
| 1,951,393 | 3/1934 | Castroviejo | 30/329 X |
| 2,599,174 | 6/1952 | Hauser | 279/41 X |
| 2,619,724 | 12/1952 | Manthey | 30/336 |
| 2,940,289 | 6/1960 | Hellwig | 294/100 X |
| 3,055,671 | 9/1962 | Lewis et al. | 279/51 |
| 3,549,159 | 12/1970 | Kroener | 279/53 |

*Primary Examiner*—Al Lawrence Smith
*Assistant Examiner*—J. C. Peters
*Attorney, Agent, or Firm*—Spencer E. Olson

[57] ABSTRACT

A knife having an easily removable blade has an elongated tubular housing having front and rear ends. An elongated stem is proportioned to fit slidably in the housing, the stem widening circumferentially in tapered fashion at the front end of the housing to define a blade-holding chuck having a blade-holding slot. The chuck is circumferentially proportioned to be compressed within the housing when the stem is slid rearwardly so as to contract the width of the slot to a blade-grasping width. A toggle lever is pivotally mounted on the stem at the rear end of the housing, the lever having a beveled edge opposing the rear edge of the housing and adapted, when the toggle lever is pivotally urged to a position essentially colinear with the housing, to contact said rear edge and forcibly slide the stem rearwardly in the housing so as to contract the blade-receiving slot. When the toggle lever is at an angle with respect to the housing, the stem is allowed to slide frontwardly in the housing so as to permit expansion of the slot to a blade-receiving width. In a preferred embodiment the rear end of the stem is ball-shaped and the toggle lever is mounted on the ball-shaped end and pivots thereon. In this embodiment the toggle lever and the ball-shaped end have aligned bores therethrough, and a pin extends through the bores for retaining the toggle lever on the stem and allowing the pivoting motion of the lever. The stem is formed of two threaded portions to facilitate assembly and adjustment of the knife.

4 Claims, 2 Drawing Figures

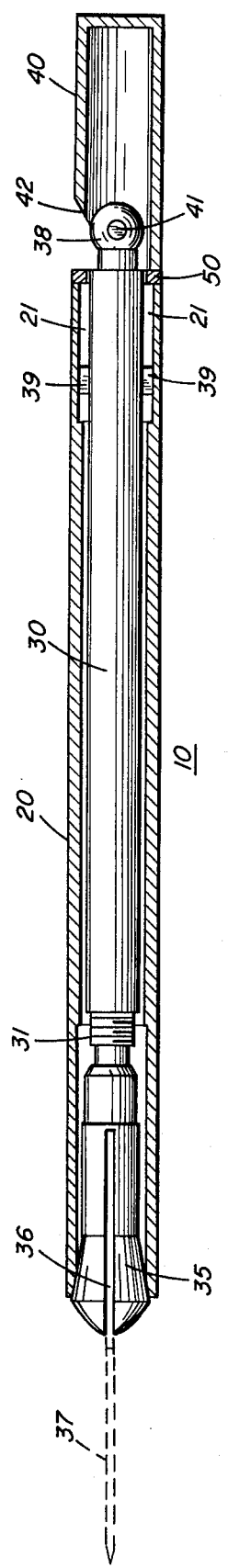

KNIFE HAVING EASILY REMOVABLE BLADE

BACKGROUND OF THE INVENTION

This invention relates to cutting tools and, more particularly, to an improved knife having a blade that is easily removable and replaceable.

There have previously been devised many types of hand-held cutting tools for use by craftsmen such as draftsmen, artists, photographers, etc. The majority of such cutting tools employ a small blade that is rigidly mounted at the end of the tool. The blade is generally mounted in removable fashion to facilitate the changing thereof, but it must be secure enough to minimize the chance of its slipping or dropping out. Typically, the end of the tool is provided with a slit into which the blade is seated and a screw-on collet compresses the slit so that the blade is grasped. This mounting arrangement requires significant time and trouble for loosening, removal, replacement, and tightening of the collet whenever the blade is to be changed. Also, the torque on the blade caused by twisting motion during use can tend to cause unwanted looseness of the collet. An example of this arrangement is shown in U.S. Pat. No. 2,569,286.

In U.S. Pat. No. 2,619,724 there is disclosed a technique wherein a blade-holding chuck is controlled by a threaded mechanism in conjunction with a spring at the rear end of the knife. A user can replace a blade by appropriate loosening or tightening of the mechanism which controls the blade-holding chuck. This technique may be somewhat faster than the conventional collet arrangement described above, but still involves screwing and unscrewing operations. The degree of tightness and rigidity is a function of human judgement and finger strength and thereby subject to error. Also, precise manufacturing tolerances of the screwing mechanism and provision for and assembly of the spring are factors in manufacturing cost and maintenance.

It is an object of the present invention to provide an improved knife wherein blade removal and replacement is extremely simple, blade rigidity is not a function of human judgement, and economies of manufacture and maintenance are realized.

SUMMARY OF THE INVENTION

The present invention is directed to an improved knife having a blade that is easily removable and replaceable. In accordance with the invention there is provided an elongated tubular housing having front and rear ends. An elongated stem is proportioned to fit slidably in the housing, the stem widening circumferentially in tapered fashion at the front end of the housing to define a blade-holding chuck having a blade-holding slot. The chuck is circumferentially proportioned to be compressed within the housing when the stem is slid rearwardly so as to contract the width of the slot to a blade-grasping width. A toggle lever is pivotally mounted on the stem at the rear end of the housing, the lever having a beveled edge opposing the rear edge of the housing and adapted, when the toggle lever is pivotally urged to a position essentially colinear with the housing, to contact said rear edge and forcibly slide the stem rearwardly in the housing so as to contract the blade-receiving slot. When the toggle lever is at an angle with respect to the housing, the stem is allowed to slide frontwardly in the housing so as to permit expansion of the slot to a blade-receiving width.

In a preferred embodiment of the invention the rear end of the stem is ball-shaped and the toggle lever is mounted on the ball-shaped end and pivots thereon. In this embodiment the toggle lever and the ball-shaped end have aligned bores therethrough, and a pin extends through the bores for retaining the toggle lever on the stem and allowing the pivoting motion of the lever. The stem is formed of two threaded portions to facilitate assembly and adjustment of the knife.

Further features and advantages of the invention will become more readily apparent from the following detailed description when taken in conjunction with the accompanying drawings.

BRIEF DESCRIPTION OF THE DRAWINGS

FIG. 1 is a cross sectional view of a knife in accordance with the invention, the knife having its removable blade shown in place; and FIG. 2 is an elevational perspective view of the knife of FIG. 1 shown in position to receive a new blade.

DESCRIPTION OF THE PREFERRED EMBODIMENT

Referring to FIGS. 1 and 2 there is shown a knife 10 in accordance with the preferred embodiment of the invention. An elongated tubular housing 20, preferably formed of aluminum, is provided with a pair of slots 21 at the rear end thereof. A cylindrical central shaft or stem 30 generally conforms to the inner diameter of the housing 20 to allow slidable insertion therein. In the present embodiment the stem 30 is formed of two pieces joined together by appropriate threading and friction fit at 31.

The front of stem 30 widens circumferentially in tapered fashion to define a blade-holding chuck which has a blade-receiving slot 36. In FIG. 1 a blade 37 is shown in dashed line as being secured in the slot 36. The chuck 35 is circumferentially proportioned to be compressed within the housing when the stem is in its rearmost position (as in FIG. 1), so that the blade is grasped tightly.

The rear of stem 30 is in the form of a ball 38 having a bore therethrough. A generally cylindrical toggle lever 40 also has a bore therethrough and is pivotally mounted on the ball 38 by a pin 41 which passes through the bores in the lever and stem. The toggle lever 40 has a beveled edge 42 which opposes the rear edge of the housing 20, said rear edge being defined by a washer 50. The washer has a square outer shape to prevent undesired rolling of the knife when laid at rest. When the toggle lever is pivotally urged to a position colinear with the housing (as in FIG. 1), the beveled "corner" of edge 42 contacts the rear edge of the housing 20 and forcibly slides the stem 30 rearwardly in the housing which, in turn, contracts the blade-receiving slot 36 as tapered chuck 35 is forced slightly into the housing. Stated another way, the toggle lever, acting via pin 41, causes the stem to be pulled rearwardly, which results in the desired contraction of slot 36 to its blade-grasping width. Since the "retaining" force is axially effected, prior problems of loosening of the blade due to the twisting thereof are eliminated.

When the toggle lever 40 is pivotally urged to an angular position from housing 20 (as in FIG. 2), the pin 41 is no longer pulled rearwardly with respect to the housing and stem 30 will slide forward somewhat due to the natural bias of the slotted tapered chuck. The slot 36 will thereby expand to a width at which an old blade can be removed and/or replaced. The stem 30 is provided with tabs 39 which seat in slots 21 and prevent rotation of the stem in the housing.

Assembly of the knife 10 is facilitated by the two piece construction of the stem 30. During assembly, the front and rear ends of the stem are respectively inserted in the front and rear ends of the housing and screwed together to a degree of proper adjustment which defines the penetration of tapered chuck 35 into the housing 20. The friction fit prevents any undesired rotation of the front portion of the stem.

The invention has been described with reference to a particular embodiment but variations within the spirit and scope of the invention will occur to those skilled in the art. For example, the stem 30 could be formed of a single piece, although this variation is not preferred.

I claim:

1. A knife having a removable blade, comprising:
   an elongated tubular housing having front and rear ends;
   an elongated stem proportioned to fit slidably in said housing;
   said stem widening circumferentially in tapered fashion at the front end of said housing to define a blade-holding chuck having a blade-receiving slot, said chuck being circumferentially proportioned to be compressed within said housing when said stem is slid rearwardly so as to contract the width of said slot to a blade-grasping width; and
   a toggle lever pivotally mounted on said stem at the rear end of said housing, said lever having a beveled edge opposing the rear edge of said housing and adapted, when said toggle lever is pivotally urged to a position essentially colinear with said housing, to contact said rear edge and forcibly slide said stem rearwardly in said housing so as to contract said blade-receiving slot, and also adapted, when said toggle lever is at an angle with respect to said housing, to allow said stem to slide frontwardly in said housing so as to allow expansion of said slot to a blade-receiving width.

2. A knife as defined by claim 1 wherein the rear end of said stem is ball-shaped and said toggle lever is mounted on said ball-shaped end and pivots thereon.

3. A knife as defined by claim 2 wherein said toggle lever and said ball-shaped end have aligned bores therethrough, and further comprising a pin which extends through said bores for retaining said toggle lever on said stem and allowing the pivoting motion of said lever.

4. A knife as defined by claim 1 wherein said stem is formed of two threaded portions to facilitate assembly and adjustment of the knife.

\* \* \* \* \*